United States Patent [19]
Pruthi et al.

[11] Patent Number: 5,980,903
[45] Date of Patent: Nov. 9, 1999

[54] COMPOSITION FOR THE TREATMENT OF VIRAL INFECTIONS INCLUDING HIV

[76] Inventors: Som C. Pruthi; Pankaj Pruthy; Jasvant Rai Pruthy, all of 2001 N. Ocean Blvd., #1602, Boca Raton, Fla. 33431

[21] Appl. No.: 09/140,838

[22] Filed: Aug. 27, 1998

Related U.S. Application Data

[63] Continuation-in-part of application No. 08/921,751, Aug. 27, 1997, abandoned.

[51] Int. Cl.⁶ ............................. A61K 35/78; A61K 9/14
[52] U.S. Cl. ...................... 424/195.1; 424/439; 424/451; 424/464; 424/405; 424/489
[58] Field of Search .................... 424/195.1, 439, 424/405, 451, 464, 489

[56] References Cited

U.S. PATENT DOCUMENTS

| | | | |
|---|---|---|---|
| 5,411,733 | 5/1995 | Hozumi et al. | 424/195.1 |
| 5,529,778 | 6/1996 | Rohatgi | 424/195.1 |
| 5,801,153 | 9/1998 | Badaway | 514/39 |

FOREIGN PATENT DOCUMENTS 0279413  10/1998  Japan .

OTHER PUBLICATIONS

Agrawal et al. Intl. J. Clin. Pharm. Ther. vol. 34, No. 9, pp. 406–409 (Abstract enclosed), 1996.

Kumari et al. Med. Sci. Res. vol. 20, No. 6, pp. 219–220 (Abstract enclosed), 1992.

*Primary Examiner*—Leon B. Lankford, Jr.
*Assistant Examiner*—Christopher R. Tate
*Attorney, Agent, or Firm*—Robert M. Downey, P.A.

[57] ABSTRACT

A composition for use in treating viral infections includes: 25%–75% Thymol (crystals of Bishop's Weed) by weight; 20%–40% fruit of Chebulic myroblan by weight; and 5%–35% leaves of Holy Basil by weight.

6 Claims, No Drawings

COMPOSITION FOR THE TREATMENT OF VIRAL INFECTIONS INCLUDING HIV

BACKGROUND OF THE INVENTION

This patent application is a continuation-in-part application of patent application Ser. No. 08/921,751 filed on Aug. 27, 1997 now abandoned.

FIELD OF THE INVENTION

The present invention relates to a composition, and more particularly, to a composition comprising natural ingredients for the treatment of viral infections, including HIV.

DETAILED DESCRIPTION OF THE RELATED ART

Viral infections present a serious threat to the health and well being of people of all ages. At present, there is no cure for viral infections and disease which results from infection. Once infected with a virus, the human body must rely on its own immune system to fight off infection. However, new types of viruses are emerging which are able to overpower the immune system and weaken the body's defenses. The Human Immunodeficiency Virus (HIV), in particular, is one such virus that has proven to be impervious to attack and is winning the battle against the human body's immune system.

Presently, millions of people around the world are HIV infected. Most of these people will suffer gradual health decline due to a weakened immune system which eventually leads to Acquired Immune Deficiency Syndrome (AIDS). This ferocious viral disease has claimed 4.5 million lives worldwide. According to government statistics, AIDS is now the leading killer of American men and women, 15 to 44 years old. HIV infection has now become an epidemic and is spreading relentlessly, threatening to claim many more millions of lives before the end of the century.

At present, the only thing that can be done is to hold off the progression of the HIV virus. There are currently over 120 drugs that have been developed by researchers in the field. Among the most promising advances in the field is a new class of medicines known as protease inhibitors. When combined with other HIV/AIDS medicines, called "cocktail" therapy, treatments using protease inhibitors have slowed the progression of HIV. This therapy, unfortunately, does not cure the patient. Further, it causes side effects which, in some cases, are unbearable. Finally, "cocktail" therapy is extremely expensive, approximately $15,000 per year (drug cost alone) for one patient.

Accordingly, there is an urgent need for an effective, less expensive means of treating viruses, including HIV, with minimal or no side effects. The present invention addresses this compelling need and provides a composition of natural herbal ingredients for treating viral infections, including HIV.

SUMMARY OF THE INVENTION

The present invention is directed to a composition for anti-viral treatment of viral diseases, including AIDS. The composition has been shown to kill viruses, including HIV, and to inhibit viral replication. The composition comprises three natural herbal ingredients including Thymol, fruit of Chebulic myroblan, and leaves of Holy Basil. Thymol is a crystal-like substance, derived from Bishop's Weed which is known botanically as Trachyspermum Ammi, and is present in an amount of between 25%–75% by weight of the composition. Chebulic myroblan is known botanically as Terminalia Chebula Retzus, and its fruit is present in the amount of between 20%–40% by weight of the composition. Holy Basil is known botanically as Ocimum Sanctum, and its leaves are present in the amount of between 5%–35% by weight of the composition.

In a preferred embodiment, the composition is manufactured in the form of capsules containing between 250 mg–1200 mg of the composition. The composition may also be manufactured as a tablet, syrup, or in a liquid form for subcutaneous injection.

With the foregoing in mind, it is a primary object of the present invention to provide a composition comprising natural herbal ingredients for the treatment of viral diseases, including AIDS.

It is still a further object of the present invention to provide a composition for the treatment of viral infections, including Human Immunodeficiency Virus (HIV).

It is still a further object of the present invention to provide a composition for treating viral infections including HIV and a method of manufacturing the composition, wherein the composition is manufactured according to a controlled process that preserves the herbal curing properties of the ingredients.

It is yet a further object of the present invention to provide a composition which kills viruses, including HIV, and which further inhibits viral replication.

It is still a further object of the present invention to provide a composition for the treatment of viral infections, including HIV, wherein the composition comprises natural herbal ingredients that have minimal or no side effects.

These and other objects and advantages of the present invention are readily apparent with reference to the following detailed description.

DETAILED DESCRIPTION OF THE PREFERRED EMBODIMENT

The composition includes the combination of Thymol crystals from Bishop's Weed, fruit of Chebulic myroblan, and leaves of Holy Basil. According to the composition of the present invention, Thymol is present in the amount of between 25% to 75% by weight of the composition, fruits of Chebulic Myroblan are present in the amount of 20%–40% by weight of the composition, and leaves of Holy Basil are present in the amount of 5%–35% by weight of the composition.

Bishop's Weed, known by the botanical name Trachyspermum Ammi, is a small annual bush with many branched leafy stems, feather-like tender leaves and flower heads. Its leaves yield crystals (called Thymol) which are known to have medicinal value in Ayurvedic practices. Chebulic myroblan is known by the botanical name Terminalia Chebula Retzus. Holy Basil, an aromatic plant, is known botanically as Ocimum Sanctum and has many branches with egg-shaped leaves that are usually smooth. Holy Basil has been known for many uses, including destroying bacteria and insects. Native to India, Holy Basil is now grown throughout the world.

The composition of the present invention is prepared by grinding Thymol (Bishop's Weed crystals) to a fine powder. Excessive grinding may result in overheating and destroying the natural properties of the herb. Therefore, it is best to grind the Thymol in a series of steps, wherein smaller particles are separated from a remainder of the particles by screening. Thereafter, the smaller particles of a predetermined maximum size are further ground and again separated, repeating this process in a series of steps to produce a fine powder. In a preferred embodiment, the process of grinding is accomplished with the use of a mortar and pestle. A series of sieves, each having predetermined sized openings in its screen, are used to separate the ground herb throughout the grinding process.

The fruits of Chebulic myroblan are first washed to remove impurities. This is done by soaking the fruit in a water filled pot which is large enough so that the volume of water is at least twice that of the fruit placed therein. After filling the pot with cool water preferably (between 65° Fahrenheit–85° Fahrenheit), the fruit is placed in the pot and soaked, while the pot is agitated to cause slight turbulence and movement of the fruit, for a period of two to three minutes. Thereafter, the water is drained and refilled with fresh, clean water in the same temperature range. This process of soaking and agitating to wash the fruit is repeated four to five times (i.e., four to five refills of fresh water in the pot). The washed fruit is then placed in boiling water for two to three minutes. Again, overheating must be avoided. The fruit is then removed from the boiling water and placed in a cool (room temperature) shady and dry area to allow the fruit to completely dry. During the drying process, direct sunlight and/or strong artificial light should be avoided. The dried fruit is then gently broken and the pit is removed. Thereafter, the dried fruit is broken into smaller pieces and ultimately ground, in a gradual procedure, over three to four steps (as set forth above) to produce a powder. As with the grinding of the Thymol, as described above, the dried fruit can be ground using a mortar and pestle with the process being broken up into a series of steps using separating sieves. Other commercially known grinding techniques may be used, including grinding machinery for mass production. In all instances, regardless of the type of grinding instrumentation and techniques used, excessive heat should be avoided to maintain the curing properties of the herbs. Accordingly, appropriate means should be employed to control heat levels throughout the grinding of the herbs (Thymol, fruit of Chebulic myroblan, and leaves of Holy Basil).

The Holy Basil plant is uprooted and its leaves are collected and washed thoroughly with cool (room temperature) water. After washing, the leaves are dried at room temperature, avoiding direct sunlight or strong artificial light, to completely remove the water and dry the leaves. The dried leaves are then ground into a fine powder, in three to four steps, in the same general manner as described above in reference to Thymol. Again, overheating must be avoided to preserve the natural healing properties, and thus separation of smaller ground particles to prevent excessive grinding, should be performed periodically through the grinding process.

All three powders (i.e., Thymol, Chebulic myroblan, and Holy Basil) are placed in a mixing chamber (e.g., a bowl or container) in accordance with their predetermined percentage by weight. The three powders are then mixed at slow speed, by stirring, until a homogeneous blend is achieved. The homogenous powder mixture is then kept in a cool, dry place until manufactured in the form of capsules, tablets, syrup, or other forms, in accordance with manufacturing techniques well known in the field. The capsules, incorporating the composition of the present invention, are preferably of a concentration of between 250 mg–1200 mg.

To treat the viral infections, the composition should be taken in dosages of between 250 mg–1200 mg. In capsule form, this may require taking one to three capsules per day, depending upon the concentration of each capsule and the prescribed dosage. The optimum dosage for most patients infected with HIV, as well as patients with other viral infections, seems to be 1500 mg per day. The capsules should be taken orally on an empty stomach with fruit juice or water. If two capsules are required, one capsule should be taken in the morning on an empty stomach and the other capsule taken in the evening, prior to an evening meal. If three capsules are required, one capsule should be taken in the morning on an empty stomach, a second capsule should be taken at noon before lunch, and the third capsule should be taken in the evening before dinner.

Improvement will ordinarily be observed in 14–21 days from the beginning of the treatment. The complete course of treatment consists of one to three capsules a day (approximately 1500 mg per day) from 8 to 12 weeks, depending on the existing disease condition. During the treatment period, spices, alcohol, meat and drugs (other than those prescribed by a physician) should be avoided.

In order to verify the effectiveness of the composition of the present invention in treating viral disorders, several test studies were performed. The studies were conducted under the supervision of a physician or a research laboratory, the results of which are set forth below.

TEST 1

In this test, a male patient suffering from shingles was administered a daily dosage of 500 mg of the composition over the course of a two month period.

In-vivo Patient Testing

Male 68 years of age

Condition: Shingles

Term of Skin disease: 3 years 7 months

Comments: Tried all available treatments, skin condition very painful

Date treatment started: May 7, 1997

Date treatment stopped: Jul. 10, 1 997

Recurrence of the disease: None in 2 months

Side effects: None

| Skin Condition (over entire body) | Before Treatment | After Treatment |
|---|---|---|
| Red spots | yes | no |
| Itching | yes | no |
| Painful to touch | yes | no |

TEST 2

In-vivo study:

This test involved the analysis of frozen blood plasma, taken from a patient infected with HIV-1 virus. The patient was being treated with the composition of the present invention, at the beginning of the test and throughout the entire testing period. The treatment consisted of a daily dosage of between 1,000 mg–1,500 mg of the composition, taken in the morning each day throughout the testing period. The frozen blood plasma of this patient was tested on two separate occasions. Prior to each testing, a blood sample was drawn from the patient. The second testing was performed approximately six weeks after the first testing.

The laboratory findings were as follows:

Date of first testing: Nov. 4, 1997

Date plasma sample received: Oct. 28, 1997
Date of draw from patient: Oct. 27, 1997
Test performed: PCR-HIV MONITOR (frozen plasma)
Date completed: Nov. 4, 1997
Report date: Nov. 4, 1997

Results of First Testing

| HIV-1 RNA copies | 176,747 copies/ml |
|---|---|

Date of second testing: Dec. 17, 1997
Date test sample received: Dec. 10, 1997
Date of draw from patient: Dec. 10, 1997
Test performed: PCR-HIV MONITOR (frozen plasma)
Date completed: Dec. 17, 1997
Report date: Dec. 23, 1997

Results of Second Testing

| HIV-1 RNA copies | 39,977 copies/ml |
|---|---|

Comments:
Two base line tests are recommended.

| Quantitation limits: | LOW | HIGH | |
|---|---|---|---|
| | 400 | −750,000 | HIV-1 RNA copies/ml |

In-vivo evaluation: Composition kills HIV virus without toxicity.

Viral load decreased from 176,744 copies/ml to 39,977 copies/ml in six weeks without any noted side effects. HIV infected patient claimed to have significant increase in quality of life.

Further observation: CD4 count increased from 98 to 132 in 30 days.

TEST 3

In-vitro evaluation:

Cytoprotection Assay for Detection of Antiviral Activity

The assay used for testing these samples for HIV antiviral activity was the Cytoprotection Assay. It is a measure of the viability of CEM-SS cells after infection with HIV and incubation in the presence of potential antiviral compounds. The cells in this assay were CEM-SS cells and the virus strain was HIV-1 RF (HTLV-IIIRF/H9).

The results were assessed microscopically.

The composition of the present invention was dissolved in methanol solvent in various concentrations and tested for HIV viral activity using the cytoprotection assay. The results were as follows:

| Mg of the Composition | 660 | 330 | 165 | 83 |
|---|---|---|---|---|
| HIV-1 antiviral protection (%) | 75 | 25 | 0 | 0 |
| Toxicity for CEM-SS cells (%) | 0 | 0 | 0 | 0 |

Observations: Composition was observed to kill HIV virus at significant levels when provided in concentrations in excess of 500 mg, without toxicity to adjacent cells.

While the present invention has been set forth in what is believed to be a practical and preferred embodiment, it is recognized that departures may be made within the spirit and scope of the following claims which, therefore, should not be limited except within the Doctrine of Equivalents.

Now that the invention has been described,
What is claimed is:

1. A composition for the treatment of viral infections including HIV, the composition comprising the following ingredients:

powder of Thymol taken from Bishop's Weed in an amount of between 25%–75% by weight of the composition;

powder of dried fruit of Chebulic myroblan in an amount of between 20%–40% by weight of the composition; and powder of dried leaves of Holy Basil in an amount of between 5%–35% by weight of the composition.

2. A method of producing a composition comprising Thymol taken from Bishop's Weed, fruit of Chebulic myroblan, and leaves of Holy Basil, said method comprising the steps of:

a) lightly grinding the Thymol to produce a first powder;

b) washing the fruit of Chebulic myroblan by soaking the fruit in a contained volume of room temperature water and agitating the water and fruit;

c) draining the water and repeating said step of washing until all impurities and contaminants are removed;

d) completely drying the fruit by placing the fruit in a dry, room temperature location out of direct sunlight and heat;

e) breaking the dried fruit into pieces and removing pits from the fruit;

f) grinding the dried fruit to produce a second powder;

g) removing the leaves of the Holy Basil;

h) washing the leaves by soaking the leaves in a contained volume of room temperature water;

i) removing the leaves from the contained volume of water and air drying the leaves in a room temperature dry location out of direct sunlight and heat to remove the water therefrom until the leaves are completely dry;

j) grinding the dry leaves to produce a third powder;

k) combining the three powders in a mixing chamber; and l) stirring the three powders until completely blended to produce a homogenous powder mixture.

3. The method as recited in claim 2 wherein said composition is contained in a capsule form comprising 250 mg–1200 mg of the said composition.

4. The method as recited in claim 2 wherein said composition is contained in a tablet form comprising of 250 mg–1200 mg of the said composition.

5. The method as recited in claim 2 wherein said composition is contained in a syrup form for oral consumption in an amount of between 250 mg–1200 mg of the said composition per teaspoon.

6. The method as recited in claim 2 wherein said composition is contained in a liquid form for subcutaneous injection.

* * * * *